(12) United States Patent
Tararuj

(10) Patent No.: US 7,348,024 B2
(45) Date of Patent: Mar. 25, 2008

(54) PULL APART FRAGRANCE SAMPLER

(76) Inventor: Christopher Tararuj, 1151 Hughes Dr., Hamilton, NJ (US) 08690

( * ) Notice: Subject to any disclaimer, the term of this patent is extended or adjusted under 35 U.S.C. 154(b) by 686 days.

(21) Appl. No.: 10/713,829

(22) Filed: Nov. 14, 2003

(65) Prior Publication Data

US 2004/0096486 A1    May 20, 2004

Related U.S. Application Data

(60) Provisional application No. 60/319,702, filed on Nov. 17, 2002.

(51) Int. Cl.
- *A61K 9/70* (2006.01)
- *A61K 9/14* (2006.01)
- *B41M 5/20* (2006.01)
- *B41M 5/24* (2006.01)

(52) U.S. Cl. .................. 424/443; 424/489; 503/200

(58) Field of Classification Search .............. 424/443, 424/489; 503/200
See application file for complete search history.

(56) References Cited

U.S. PATENT DOCUMENTS

| | | | | |
|---|---|---|---|---|
| 3,685,734 A | * | 8/1972 | Paciorek et al. .............. 239/56 |
| 3,943,063 A | * | 3/1976 | Morishita et al. ......... 427/213.36 |
| 4,751,934 A | * | 6/1988 | Moir et al. ................... 132/319 |
| 4,874,129 A | * | 10/1989 | DiSapio et al. ................ 239/36 |
| 4,908,233 A | * | 3/1990 | Takizawa et al. ........ 427/213.35 |
| 4,925,517 A | * | 5/1990 | Charbonneau et al. ...... 156/276 |
| 4,988,557 A | * | 1/1991 | Charbonneau .............. 428/204 |
| 5,246,603 A | * | 9/1993 | Tsaur et al. .................. 510/519 |
| 5,248,537 A | * | 9/1993 | Giannavola ................ 428/40.2 |
| 5,566,693 A | * | 10/1996 | Gunderman et al. ......... 132/333 |
| 5,591,146 A | * | 1/1997 | Hasse .......................... 604/359 |
| 5,782,060 A | * | 7/1998 | Greenland ................... 715/840 |
| 5,827,913 A | * | 10/1998 | Baetzold et al. ............. 523/210 |
| 6,454,842 B1 | * | 9/2002 | Vernardakis et al. ...... 106/31.02 |
| 6,723,671 B2 | * | 4/2004 | Zolotarsky et al. ......... 442/417 |
| 2005/0026800 A1 | * | 2/2005 | Broeckx et al. ............. 510/276 |

* cited by examiner

*Primary Examiner*—Sharon Kennedy

(57) ABSTRACT

Economical and improved pull apart fragrance sampling device constructed of a film to film laminate. The mechanism for release of fragrance is accomplished by providing a microcapsule layer between a top ply and a bottom ply, which upon drying holds the overlying plies together, the microcapsules rupture upon peeling the top ply from the bottom ply, the fragrance is thereby released. A sampler produced as disclosed provides greater stability and shelf life than a paper sampler product while dramatically reducing manufacturing and raw material costs due to it's construction. The sampler provides the maximum flexibility in use and manufacture at a minimum cost.

11 Claims, No Drawings

PULL APART FRAGRANCE SAMPLER

Applicant is claiming the benefit of Provisional Application Nos. 60/319,702 filed Jan. 17, 2002

FEDERAL SPONSORED R&D

Not Applicable

REFERENCES CITED

| | | | |
|---|---|---|---|
| 4606956 | August 1986 | Charbonneau et al. | 428/40. |
| 4874129 | October 1989 | DiSappio et al. | |
| 4880690 | November 1989 | Szycher et al. | 442/304 |
| 4925517 | May 1990 | Charbonneau et al. | 156/276 |
| 4925667 | May 1990 | Fellows et al. | 424/64 |
| 4940584 | July 1990 | Tararuj et al. | 424/401 |
| 4952400 | August 1990 | Tararuj et al. | 424/401 |
| 4988557 | January 1991 | Charbonneau | 428/204 |
| 5391420 | February 1995 | Bootman et al. | 428/195. |
| 5439172 | August 1995 | Comyn et al. | 239/34 |
| 5562112 | October 1996 | Gunderman et al. | 132/333. |
| 5566693 | October 1996 | Gunderman et al. | 132/333. |
| 5622263 | April 1997 | Greenland | 206/581. |
| 5637401 | June 1997 | Berman et al. | 252/315 |
| 5645161 | July 1997 | Whitaker et al. | 206/0. |
| 5782060 | July 1998 | Greenland | 345/840 |
| 5817385 | October 1998 | Stanislav | 428/40.2 |
| 5885701 | March 1999 | Berman et al. | |
| 5928748 | July 1999 | Jones et al. | |
| 5985821 | November 1999 | Dobler et al. | 512/2 |
| 6062235 | May 2000 | Renna | 132/320 |
| 6099858 | August 2000 | Morton et al. | 424/456 |
| 6125614 | October 2000 | Jones et al. | |
| 6251408 | June 2001 | Dobler | 424/400. |
| 6287652 | September 2001 | Speckhals et al. | 428/35.2 |
| 6301860 | October 2001 | Gunderman et al. | 53/410 |
| 6326069 | December 2001 | Barnett et al. | 428/35.7 |
| 6364097 | April 2002 | Whitaker et al. | 206/5 |
| 6403186 | June 2002 | Tararuj et al. | 428/40.1 |
| 6461620 | October 2002 | Dobler | 424/400 |

BACKGROUND OF THE INVENTION

The most widely used and most economical method for sampling fragrances is a paper to paper laminate containing microencapsulated fragrance oil and an adhesive/binder to adhere the capsules to the paper. This laminated construction is easily separated, breaks the capsules efficiently and quickly releases the fragrance upon opening. This process must however, be carefully controlled to apply just the right amount of material, and formulated with precisely the right amount of binder/adhesive so that the lamination opens properly without adhering too tightly or not adhering enough. The manufacture of this type of sampler is highly complex for many reasons, not the least of which are that the binder/adhesive and paper must be carefully and judiciously controlled so as not to adversely effect function and the fragrance fidelity. The printing and converting of this type of sampler is also not well suited for short runs or advertisers requiring multiple fragrances. Another drawback has been that no printing or associated graphics can be utilized in the fragrance sample area. To address one of these shortcomings Jones U.S. Pat. Nos. 5,928,748 and 6,125,614 have disclosed a polymeric film laminated over the graphics allowing the fragrance to be subsequently applied over the film without any adverse effect on the printing. Other than sweeping generalities, some of which suggest using straight perfume or encapsulated material, no suitable means is suggested for applying and protecting the fragrance so that the sampler will have a sufficient shelf life and release the fragrance only upon opening. Comyn U.S. Pat. No. 5,439,172 has disclosed a similar construction in label form which relies on absorption of the fragrance into the film, this construction is dependent on the vapor barrier properties of the polymer film to protect the fragrance during it's life cycle, upon opening the sealed unit, the exposed surface provides a means for the fragrance to volatilize into the atmosphere. While this construction provides for a very visually appealing sampler, the shelf life and stability tends to be limited. Generally this construction is not well suited for high speed and economical manufacture and fails to provide adequate burst or intensity.

U.S. Pat. No. 6,403,186 discloses a gelatenoid product that relies on a microencapsulated fragrance in a gel vehicle. The product must be applied to the skin in order to break the capsules and release the fragrance, thus a consumer may be reluctant to apply the fragrance if they cannot adequately smell the fragrance first. To compensate for the lack of burst, this patent discloses that a portion of the fragrance may be dispersed in the non volatile gelatenoid vehicle, the non volatile vehicle engulfs and provides a measure of protection for the volatile fragrance oil during it's life cycle, this allows the fragrance to burst upon opening of the sampler so the consumer can smell the fragrance before applying. This method does not provide for long term stability and shelf life of the burst, particularly when the sampler is subjected to elevated temperature and humidity.

U.S. Pat. No. 4,925,517 discloses coating a substrate with a water soluble coating and drying the coating, a slurry of microcapsules is then coated over the dried coating. The capsules reactivate the adhesive properties of the coating and consequently stick to the coating, upon pulling the two plies apart the capsules rupture and release the fragrance. Another U.S. Pat. No. 4,988,557, discloses a similar construction except that at least some of the area is not coated with a reactivatable adhesive and these capsules do not rupture upon opening. These methods have the disadvantage of needing to apply two coatings and drying the first coating which slows the process considerably and increases energy as well as significantly adding to manufacturing costs.

Several other patents disclose a variety of constructions for fragrance sampling including: U.S. Pat. Nos. 4,874,129, 4,880,690, 4,952,400, 4,940,584, 5,391,420, 5,566,693, 5,622,263, 5,637,401, 5,645,161, 5,782,060, 5,885,701, 6,251,408, 6,301,860, 6,326,069, and 6,364,097. Some of these provide for an air tight sampler which holds a fragrance and alcohol or silicone mixture, upon opening, the fragrance can be evaluated and if desirable can be applied to the skin for extended trial. While these are functional sampling means they tend to be very expensive and thus have not been widely used, particularly by advertisers of low unit cost products. Many more patents teach a wide array of encapsulation methods and techniques but to date a reliable and inexpensive method does not exist for mass producing a fragrance sampler that could be reliably utilized by advertisers of low end products as well as high end expensive perfumes.

BRIEF SUMMARY OF THE INVENTION

Thus a need exists for an economical, versatile and reliable method for producing a fragrance sampler that provides visual aesthetics, bridges the economy of scale and cost for small and large users and assures adequate fidelity of the fragrance being sampled. The disclosed invention may be practiced with a traditional microencapsulation widely used in the industry. The gelatin/Gum Arabic coacervation system is the most widely used, probably because the ingredients are relatively safe and the process is gentlest on the microencapsulate. Gelatin based capsules thus would be an ideal choice if a reliable means could be developed to insure adhesion to a polymeric film and upon drying and subsequent separation of the plies, the capsules would rupture releasing the fragrance oil contained therein. Ideally without the need for adhesives/binders and secondary coatings which could adversely effect the fragrance. While enapsulatated material has heretofore been coated between polymeric films, no capsule breakage or means for capsule breakage has been provided. Various adhesives and coatings have been suggested but no viable means currently exists. The films simply peel part, and since a sufficient bond is not provided, the capsules remain virtually intact and unbroken, diffusion from the capsules accounts for any perceived odor upon opening. The choice of polymer films is also critical and thus the most preferred materials tend to be those with the greatest chemical resistance to the fragrance oil. Fragrance oils tend to be very active solvents and generally have a deleterious effect on polymers. The Comyn patent takes advantage of such properties and teaches that fragrance oil can be forced into the polymeric matrix of polyester with the aid of a suitable organic solvent, this limited penetration is then halted upon evaporation of the solvent or others means and the fragrance oil is subsequently sealed in upon application of a second ply of polyester and an adhesive. Other patents and patent applications such as Speckhals et al. patent application Ser. No. 2001009175 and U.S. Pat. No. 6,287,652 also specify polymers which posses superior barrier properties and chemical resistance. Polypropylene is specifies in U.S. Pat. No. 6,403,186 as being highly preferred primarily due to its low cost, the fragrance life of the non microencapsulated portion is thus sacrifices due to polypropylene's relatively poor vapor containment properties. Some polymers posses vapor barrier properties approaching glass or aluminum, but today these tend to be prohibitively expensive. Thus with these restrictions in mind it is difficult to provide for an easily manufactured and inexpensive sampler that will provide the rigorous needs of a fragrance sampling devise.

DETAILED DESCRIPTION

Among the least costly polymers available is polystryrene. Unfortunately most fragrance oils will very quickly destabilize and even dissolve polystyrene. The vapor barrier properties of polystyrene are also inferior. If a fragrance is coated over polystyrene and covered with another layer of polystyrene the resulting laminate, after aging, cannot be separated without tearing the film. The fragrance also quickly migrates through the film and into the environment. Surprisingly, when polystyrene is coated with gelatin base microcapsules, a functional bond develops between the walls of the microcapsules and the polymeric film. When the capsules are sufficiently dry, this bond is strong enough to prevent the capsules from peeling away from the polystyrene film upon separation of the plies. The opposing layers can however, be separated easily as the bond is only as strong as the tensile strength of the capsule. The result is that the capsules fracture upon opening and release the encapsulated material into the environment.

Even more surprising, the polystyrene appears to acts synergistically with the walls of the capsules providing superior resistance to diffusion of the encapsulated material through the wall of the capsule. Generally low crosslink density microcapsules like those made with gelatin have poor high humidity stability, in particular at elevated temperature. The encapsulated material tends to diffuse through the walls of the capsule at a relatively high rate. Thus the art has many well known suggestions for methods of improving this problem, including coating the paper with various coatings such as polyvinyl alcohol and various capsule wall cross linking methods to provide for a more effective barrier to diffusion in particular at elevated temperature and humidity. Among the most effective of these is the use of plastic capsules, for example urea formaldehyde or melamine formaldehyde, or any wall materials of a much higher crosslink density such that diffusion does not occur or is substantially reduced. Thus when polystyrene is coated with gelatin based capsules, the combination results in significantly improved high temperature and humidity stability.

Preodor is common problem with traditional fragrance samplers. Consumers often complain that their magazines, catalogs or other mailed articles smell as a result of the samplers that they contain. Although the problem has largely been blamed on broken and leaking capsules, the fact that fragrances will diffuse through a gelatin based capsule cannot be dismissed. Polystyrene, while not a superior barrier film, dramatically reduces diffusion of fragrance from a gelatin based capsule. Thus another solution is provided by the present invention. The sampler as disclosed eliminates preodor issues.

Typically, microcapsules in the 15-50 micron range are used for snap apart paper samplers, most preferred size being 20-35 microns. This also appears to be a suitable range for optimum practice of the disclosed invention. Capsules as small as 1-10 have also been tested and appear to function in accordance with the present invention but as expected the intensity of burst is diminished significantly as a result of fewer broken capsules and generally lower payload volume contained in smaller capsules. Larger capsules, 70-125 microns, have also been evaluated but significant deterioration of the polystyrene film becomes evident, probably as a result of capsule breakage due to their large size. The phase ratio or wall to capsule fill ratio appears to have a minimal effect on bonding properties, typical formulations with 5-20% wall appear to perform well. As little as 0.75% wall is sufficient to produce a functional sampler. As much as 35.0% wall has also been evaluated and also appears to function as desired except that a longer drying time is required. Thus the highly preferred capsule particle size is 25-40 microns, and the wall constitutes 3-15% based on the encapsulated material.

Some fragrances may have no effect on the polystyrene film. In this case an additive may be included in the candidate encapsulate material to promote adhesion to the film. While this aspect has not been fully investigated it will be obvious to one skilled in the art as to which materials would provide for desirable results.

Slurry compositions with and without adhesive/binder additives have been tested and both function adequately. The binder system is thus not necessary and further improves the product since binders potentially add odors that often cause olfactory issues. Thus a typical microcapsule as currently used in the art not only functions within the scope of this invention but performance properties of such capsules actually benefits.

A novel means for sampling fragrance is hereby disclosed, in effect a clear snap apart fragrance strip, functioning much the same way as traditional paper samplers. The invention also greatly improves performance properties of standard encapsulation systems, especially gelatin/gum Arabic systems, which are most preferred and most widely used by current producers and the need for adhesives and binders is eliminated. The invention also functionally eliminates preodor. The disclosed construction may also be manufactured as an integral part of a consumer product label. Thus a label on a shampoo, deodorant or any consumer product could be used as a vehicle for promoting another product without requiring a second label or any other carrier. Department store remit envelope manufacturers can also easily utilize the disclosed invention. Window patching equipment can be utilized to apply the film and any suitable means can be subsequently used to apply the fragrance capsules, including spraying, intermittent extrusion, etc. This flexibility in application is significant because typical sampler coating weights and uniformity of coating must be carefully controlled to prevent fiber tear and insure proper sampler function, the disclosed invention does not require a uniform and precise application to insure functionality. Thus the most dramatic effect of the disclosed may be the opening of new market segments which could not historically afford to sample fragrances and addition of new manufacturing processes to produce economical samplers.

EXAMPLES

In each of the following examples a cost weight of about 6-16 grams per square meter was applied to a two mil thick (0.002 inch) uncoated polystyrene film and covered with a second layer of two mil polystyrene typically used in the label converting industry. Coated samples were subjected to 90% relative humidity at 40 degrees Celsius for three weeks. These samples were then evaluated against a control for olfactory fidelity and functionality.

Example #1

A typical formulation used for coating on paper samplers was used. The slurry contained 20% capsules and typical loading of adhesive/binder. The vast majority of the capsules ranged 15-40 microns in diameter. The capsules were made using a typical formulation consisting of a gelatin and gum Arabic coacervate, crosslinked with glutaraldehyde. The capsules had 15% wall based on the weight of the internal phase (encapsulate). Results were satisfactory.

Example #2

Same capsules were used as in example 1, but no binder or any other additives were added. The capsule concentration was increased to 35%, balance was only water. Results were satisfactory, coating was somewhat difficult due to viscosity/rheology of the slurry. Results were satisfactory.

Example #3

Same capsules were used as in example 2, but capsule concentration was decreased to 30%, additionally viscosity was modified for optimum performance properties more conducive to flexographic or silk screen application. Results were satisfactory.

Example #4

Capsules were made as in example # 1, 15% wall, using a formulation consisting of gelatin and gum Arabic coacerbate, crosslinked with glutaraldehyde, but the capsule size was reduced to a range of I-15 microns in diameter, the majority of the capsules were 5-10 microns. The capsule concentration was 25%, the visocsity was modified for optimum machinability properties. Results were satisfactory, but burst and intensity was noticeably decreased, even initially.

Example #5

Capsules were made as in example #4, 15% wall, using a formulation consisting of gelatin and gum Arabic coacervate, crosslinked with glutaraldehyde, but the capsule size was increased to a range of 70-125 microns in diameter. Capsule concentration was 35% and the viscosity was modified for optimum machinability properties. Results were satisfactory, but deformation and tearing of the film is noted on both ambient and aged samples.

Example #6

Capsules were made as in example #5, but the wall constituted 0.75% based on the internal phase, capsule loading was left at 35%, capsule diameter was made at 20-45 microns. The viscosity was modified to optimize machinability. Results were satisfactory.

Example #7

Capsules were made as in example # 6, but the wall was adjusted to 3%, capsule loading was left at 35% and viscosity was modified. Results were satisfactory.

Example #8

Capsules were made as in example #6, but the wall was adjusted to 5%, capsule loading was left at 35% and viscosity was modified. Results were satisfactory.

Example #9

Capsules were made as in example #6, but the wall was adjusted to 7%, capsule loading was left at 35% and viscosity was modified. Results were satisfactory.

Example #10

Capsules were made as in example #6, but the wall was adjusted to 12%, capsule loading was adjusted to 25% and viscosity was modified. Results were satisfactory.

Example #11

Capsules were made as in example #6, but the wall was adjusted to 20%, capsule loading was adjusted to 30% and viscosity was modified. Results were satisfactory.

Example #12

Capsules were made as in example #6, but the wall was adjusted to 35%, capsule loading was adjusted to 30% and viscosity was modified. Results were satisfactory, drying time was noticeably longer.

Example #13

Capsules were made with a melamine formaldehyde formulation with 10% wall. A final slurry containing 35% capsules in water was coated as in the other examples. The capsules did not adhere to the film sufficiently to cause capsule breakage upon opening. The capsules were easily removed as a free flowing powder by light fingertip pressure from the film. Results were unsatisfactory.

Example #14

Capsules were made with a urea formaldehyde formulation with 10% wall. A final slurry containing 35% capsules was adjusted to the desired viscosity and coated as in the other examples. These capsules also did not adhere to the film sufficiently to cause capsule breakage upon opening. The capsules were easily removed by light fingertip pressure from the film. Results were unsatisfactory.

Example #15

Capsules were made with a polyurea encapsulation procedure with 10% wall. A final slurry containing 40% capsules was adjusted to the desired viscosity and coated as in the other examples. The capsules did not adhere to the film sufficiently to cause capsule breakage upon opening. The capsules could not however be removed by light fingertip pressure from the film. Results were unsatisfactory.

Various modifications to the capsules and polystyrene film may be made to alter the ultimate makeup of the sampler and improve function without departing from the original spirit of the invention. For example the use of other types of microcapsules that have some inherent degree of permeability, including those made by various methods of simple or complex coacervation, interracial and in situ polymerization, polycondensation, and comprised of materials and combinations including gelatin, gum Arabic, alginates, carrageenam, CMC (carboxymethylcellulose), PVM/MA, EMA, polyphosphate, polyurea, etc. It may also be possible to coat the capsules with a material that would act as a solvent on polystyrene, or conversely to coat a polystyrene or other suitable material over any conventional polymeric film and achieve the desired results.

The invention claimed is:

1. A pull apart device comprising:
   a top portion having an inside surface comprising polystyrene, a polystyrene blend or a polystyrene coated substrate,
   a bottom portion having an inside surface comprising polystyrene, a polystyrene blend or a polystyrene coated substrate; and
   a gelatin-based microcapsule layer deposited by conventional means onto an inside surface of either the top or bottom portion, wherein the microcapsules adhere to the bottom and top surfaces such that the capsule coating bonds the overlying surfaces together, the bond between the top and bottom surfaces can be broken by separating the plies, whereby the microcapsules are substantially compromised and release a material contained therein.

2. A pull apart device according to claim 1, wherein the microcapsule coating contains other additives.

3. A pull apart device according to claim 2, produced in the form of a pressure sensitive backed label which may be affixed to any printed matter, packaging or any delivery vehicle.

4. A pull apart device according to claim 2, distributed in the form of a laminated card manufactured in a single or multiple operation with or without the need for subsequent affixing to another delivery vehicle.

5. A pull apart device according to claim 2, wherein the polystyrene surface is over-laminated with a polymeric, paper or composite stock including metalized films, holographic films or preprinted stock.

6. A pull apart device according to claim 4, wherein a single continuous polystyrene substrate is folded over onto itself before or after laminating to another substrate such as a paper of film.

7. A pull apart device according to claim 2, wherein the microcapsules contain a fragrance, which is released upon separation of the overlying plies.

8. A pull apart device according to claim 2, wherein the additives comprise adhesives and viscosifiers.

9. A pull apart device comprising:
   a first ply having an inside surface comprising a coated paper,
   a second ply having an inside surface comprising polystyrene, a polystyrene blend or a polystyrene coated substrate; and
   a microcapsule layer comprising microcapsules which are made with a wall material having at least some degree of permeability deposited by conventional means onto an inside surface of either the top or bottom portion, wherein the microcapsules adhere to the bottom and top surfaces such that the capsule coating bonds the overlying surfaces together, the bond between the top and bottom surfaces can be broken by separating the plies, whereby the microcapsules are substantially compromised and release a material contained therein.

10. A pull apart device comprising:
    a top portion having an inside surface comprising polystyrene, a polystyrene blend or a polystyrene coated substrate,
    a bottom portion having an inside surface comprising polystyrene, a polystyrene blend or a polystyrene coated substrate; and
    a microcapsule layer comprising microcapsules made with a wall material having at least some degree of permeability deposited by conventional means onto an inside surface of either the top or bottom portion, wherein the microcapsules adhere to the bottom and top surfaces such that the capsule coating bonds the overlying surfaces together, the bond between the top and bottom surfaces can be broken by separating the plies, whereby the microcapsules are substantially compromised and release a material contained therein.

11. A pull apart device according to claim 1, wherein the gelatin based microcapsule layer is a coacervate of gelatin and at least one material selected from the group consisting of gum arabic, polyphosphate, alginate and carboxymethylcellulose.

* * * * *